US006800015B1

United States Patent
Derges

(10) Patent No.: US 6,800,015 B1
(45) Date of Patent: Oct. 5, 2004

(54) SCENTED WAXED PLUSH TOYS

(76) Inventor: Patricia A. Derges, 601 E. South St., Ozark, MO (US) 65721

( * ) Notice: Subject to any disclaimer, the term of this patent is extended or adjusted under 35 U.S.C. 154(b) by 0 days.

(21) Appl. No.: 10/395,044

(22) Filed: Mar. 20, 2003

Related U.S. Application Data

(60) Provisional application No. 60/366,862, filed on Mar. 21, 2002.

(51) Int. Cl.[7] .................................................. A63H 3/02
(52) U.S. Cl. ....................................... 446/369; 239/211
(58) Field of Search ............................. 446/369, 71–77, 446/268, 385; 119/711, 707; 239/211, 289

(56) References Cited

U.S. PATENT DOCUMENTS

| 5,676,583 A | 10/1997 | Wang et al. | 446/268 |
| 6,012,963 A | 1/2000 | Lee | 446/385 |
| 6,089,947 A | 7/2000 | Green | 446/268 |

Primary Examiner—Jacob K. Ackun
Assistant Examiner—Jamila Williams
(74) Attorney, Agent, or Firm—Jonathan A. Bay

(57) ABSTRACT

A plush article is given a coating of wax which is imbued with a scent substance that diffuses slowly over time. That way, this coated scented plush article doubles not only as an ornamental accessory but also as a disguised air freshener.

18 Claims, 3 Drawing Sheets

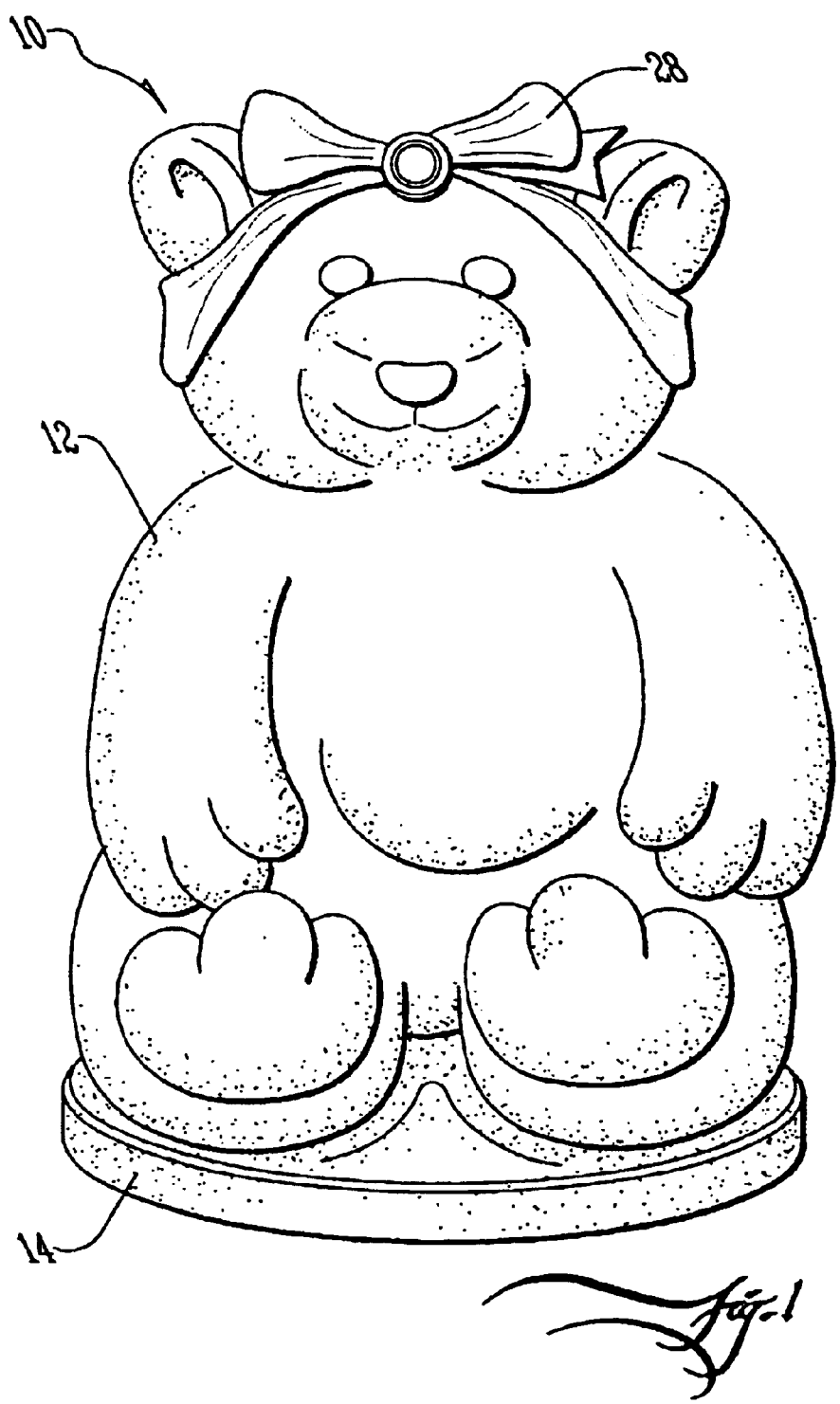

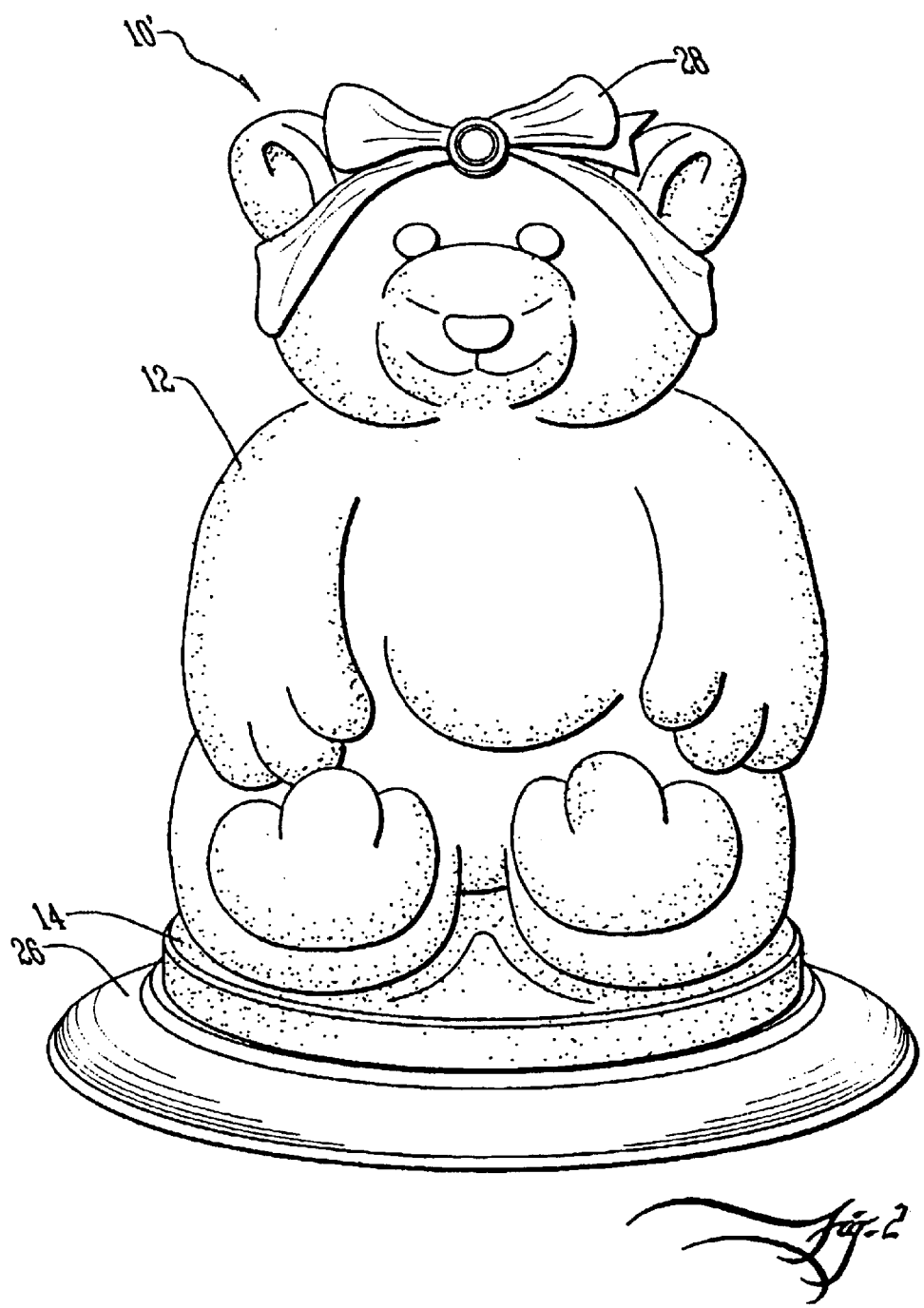

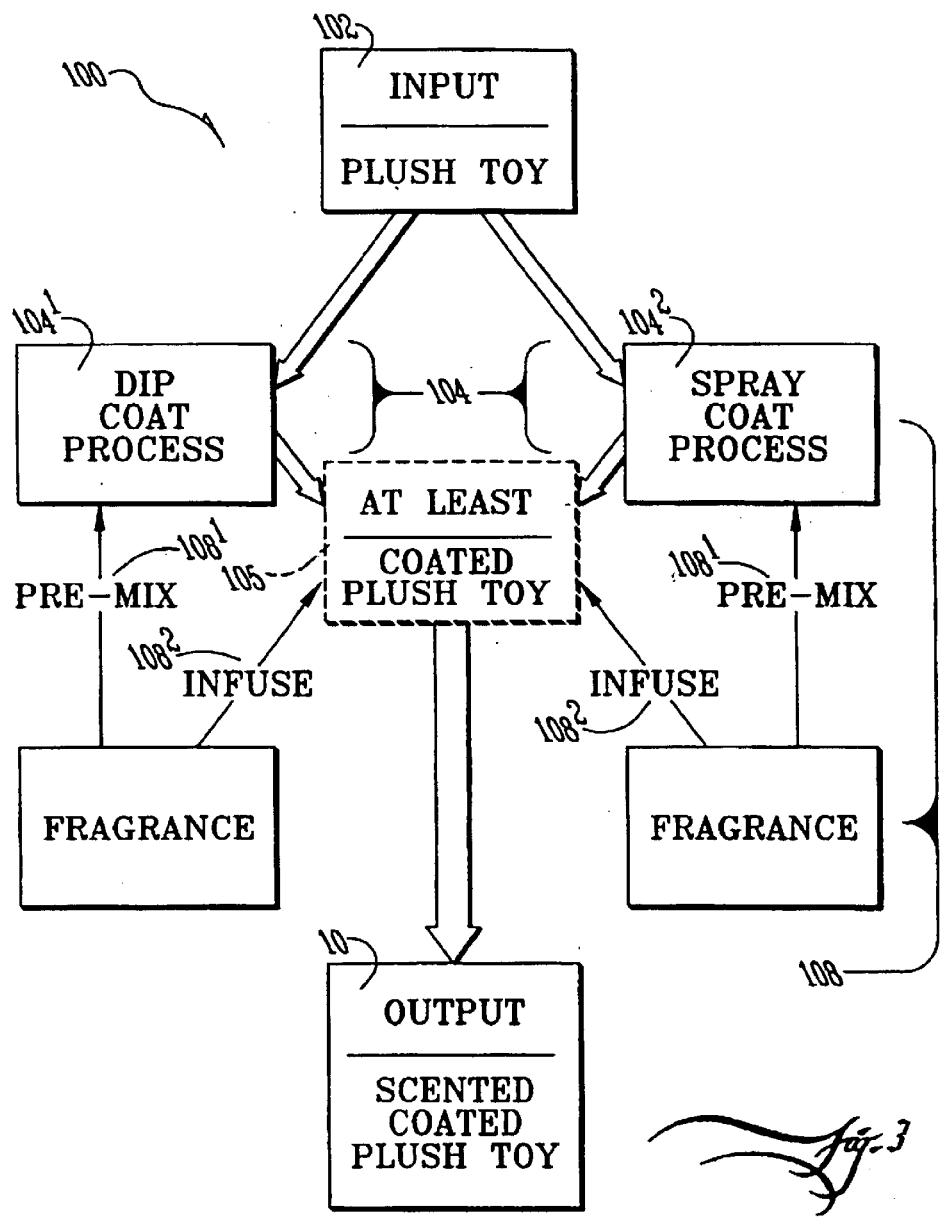

SCENTED WAXED PLUSH TOYS

CROSS-REFERENCE TO PROVISIONAL APPLICATION(S)

This application claims the benefit of U.S. Provisional Application No. 60/366,862, filed Mar. 21, 2002, which provisional application is incorporated herein in full by this reference.

BACKGROUND AND SUMMARY OF THE INVENTION

The invention relates to air fresheners and more particularly to scented waxed plush toys.

It is an object of the invention to provide an air freshener disguised as a plush toy.

It is an alternate object of the invention to provide an air freshener disguised as an accessory for decorating or otherwise gracing or humoring a room or office or like space.

It is another object of the invention to provide a method for producing scented waxed plush articles in which economy and simplicity are paramount.

These and other aspects and objects of the invention are provided in a plush article having a coating of wax which is imbued with a scent substance that diffuses over time. That way, such a coated scented plush article thereby doubles as an ornamental accessory as well as a disguised air freshener. Optionally the wax can be selected from any of and without limitation beeswax, carnauba wax, paraffin wax, soy wax, liquid wax, pillar wax, and/or granular wax. Likewise, the scent substance can be selected from and without limitation any of essential oils, perfume oils, alcohol- or glycerin-based extracts, and/or finely pulverized solid materials including any of salts, hard resins, wood chips, and/or wood dust.

Preferably, the plush article originally comprises a soft casing, like that stuffed with an infill material, and which soft casting preferably has a velvety, fuzzy or furry finish, because this affords the wax coating better opportunity to adhere securely thereto. During the process of producing the coated scented plush article, it preferably is produced with a thick wax base layer. The thick wax base layer not only provides a flat bottom for resting the article on a planar support surface (eg., book shelves or cabinet tops) but also adds weight and hence provides the plush article with a low-center of gravity, and thus stability, for propping up the plush article in a given posture or other position of repose. Indeed, if the wax coating is a "hard" coating, such then immobilizes the plush toy in a more or less permanent posture or position of repose.

Aspects of the inventive method for producing the above-sketched scented waxed plush article include the following. Briefly, a plush article is coated in the wax, and the wax is imbued (including without limitation by any of the example ways given below) with a scent substance that diffuses its scent slowly over time such that, as desired, the scented waxed plush article doubles as an ornamental accessory as well as an air freshener.

The step of coating optionally comprises this approach to the matter. That is, at some original time a stock supply of hard wax is warmed to obtain elevated-temperature liquified wax, which is then applied to the plush article to coat in such elevated-temperature liquified wax. Then, the resulting coated plush article is set aside in a chosen posture or position of repose to both cool and hence be immobilized or "frozen" in the chosen posture or position of repose as the elevated-temperature liquified wax consequently hardens.

The steps of coating and scenting can be combined and intertwined in various ways. For example, the step of coating might be undertaken either by dipping the plush article in liquified wax or else spraying on liquified wax onto the plush article. The plush article is optionally coated in whole or in part whether by dipping or spraying.

The step of imbuing the wax with the scent substance can be achieved either by premixing the scent substance with wax before the step of coating or alternatively, after the step of coating, by infusing the scent substance in the wax at elevated temperature. Elevating the temperature of the wax makes it better at accepting the infusion of the scent substance.

The coating step might immediately yield a plush article dripping with runny hot wax. This can be taken advantage of by positioning such in a given position of repose on a planar work surface and allowing a thick wax base layer to pool around and harden such that the end-product scented waxed plush article is provided with a flat bottom for setting on planar support surfaces and a weighted base providing a low-center of gravity and hence stability for propping up the plush article in the given position of repose.

Other options with the coating step might include elevating the temperature of solid wax to obtain liquified wax and then coating the supplied plush article with such elevated-temperature liquified wax. That way, the step of imbuing the wax with the scent substance might combine a step of allowing the elevated-temperature wax coating to cool concurrently with a step of infusing the cooling wax coating with the scent substance. The infusing step might be achieved by spraying an aerosol or liquid form of the scent substance onto the cooling wax.

The plush article in its original design can be of about anything, whether of nature or pure abstraction, including any designs realistically or otherwise imitating a plant, animal or human form. After production, the plush article might be further adorned in wearing apparel or other accessories. Long after production, indeed after an extended aging period following final production, the owner of the scented waxed plush article can reinvigorate the scent-diffusion power of the scented wax by mildly warming up the wax of the coating. This can be achieved as simply by using a conventional hair dryer. A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings, FIG. 1 is a pictorial view of a scented waxed plush toy in accordance with the invention;

FIG. 2 is a pictorial view comparable to FIG. 1 except showing an alternate embodiment of the scented waxed plush toy thereof disposed on a sub-base; and FIG. 3 is a block diagram schematic of a process in accordance with the invention for producing such inventive, scented waxed plush toys.

DETAILED DESCRIPTION OF THE PREFERRED EMBODIMENTS

FIG. 1 shows a scented waxed plush toy 10 in accordance with the invention. FIG. 2 shows an alternate embodiment 10' thereof disposed on a sub-base 26. The inventive product 10 operates without limitation as a home or office accessory for ornamentation or amusement purposes and the like as well as operates as a scent releaser for air freshening or scenting purposes as well. Whereas the views show teddy bear versions of the invention, this is done so for convenience in this description and does not limit the invention to "teddy bear" plush toys only, as the inventive product 10 and inventive process 100 (see FIG. 3) for production thereof can be applied to other suitable plush articles 10 as well and without limitation.

Plush articles 10 comprise a class of articles known in the art. They are typified by soft-sided stuffed animals, figures (eg., of human form) or other designs. The soft sides (or "casings") can comprise any various suitable materials for the purpose including without limitation natural or synthetic textiles, meshes, furs or hides (eg., chamois). Very often, the soft casings of a plush article characteristically include a velvety, fuzzy or furry aspect and this includes without limitation a pile (eg., a textile feature of usually short close filaments that may be obtained by an extra set of filling threads or yarns originally raised into loops and then cut or sheared). It is an aspect of the invention that such a velvety, fuzzy or furry aspect of the plush article 10 affords for better adherence of the wax or wax-like coating 12 described more particularly below.

The soft casings of the plush articles 10 can be produced as somewhat a sack or sock stuffed with an infill material comprising either one main compartment or a set of partitioned sub-compartments. The articles 10 may be plush in part only and incorporate diverse other construction components such as joints for figures or toys and the like. The preferred kinds of infill material for stuffing such articles 10 includes without limitation such suitable materials as beans or other natural and synthetic pellets, seeds, sawdust, corncob, straw (and/or grass, such as excelsior grass), polyfill or fiberfill among others.

It is an aspect of the invention to coat these kinds of plush toys or articles 10 in a wax or wax-like coating 12. Non-limiting examples of suitable materials for the coating 12 include beeswax, carnauba wax, paraffin wax, soy wax, liquid wax, pillar wax, granular wax, or any other substance having the relevant properties for forming a layer or coating over a surface and concurrently hold a scent in a variety of forms of application to such surface. The preferred end goal is to achieve a coating 12 on the plush article 10 in whole or in part, wherein the coating 12 is imbued with a fragrance or scent substance (eg., indicated as 106 in FIG. 3) that can diffuse out over time and provide a room or like space with a fresh or fragrant scent. Persons detecting such scent(s) or fragrance(s) are thereby pleased or amused with the end result. Whatever is any person's true reaction to the scented coated plush article 10 in accordance with the invention, such reaction corresponds more or less to the same reaction achieved by unlit scented or fragrant candles. Indeed, in the case of candles, the scent or fragrance emanating therefrom is comparably as potent without ever actually lighting the candle, or burning the wax.

FIG. 1 shows a teddy bear version of a scented waxed plush article 10 in accordance with the invention which is coated with a coating 12 in whole and not as alternatively otherwise as advantageous as merely in part. Other effects such as the knotted head band 28 shown in the view or the like can be added after the coating 104 and/or coating and scenting processes 104 and 108, as more particularly described below in connection with FIG. 3. In this FIG. 1's version 10 of the invention, the scented waxed plush article 10 is furthermore characterized by a thick wax base layer 14.

The thick wax base layer 14 is a production result of one way of producing the product 10 in accordance with the invention. It is an aspect of the invention that the scented wax plush article 10 can be produced in ways to eliminate the thick base layer 14. However, in some versions of the invention the thick wax base layer 14 is desirable, as it provides a low-center of gravity and hence stability for propping up the scented wax article 10 in a given posture or other position of repose. In contrast, in other versions of the invention (not shown in either FIG. 1 or 2) it is equally desirable to eliminate the thick base layer 14. Elimination of any thick base layer 14 can be achieved in various ways described more particularly below in connection with FIG. 3.

FIG. 2 shows a comparable, thick-base version 10' of the invention disposed on a sub-base 26 or, more accurately in terms of FIG. 2, an inverted plate. The sub-base 26 is preferred in cases where the materials used for the coating 12 or else the scenting substance 106 might contain compounds such as acids that can cloud the finish of the ultimate support surface (eg., book shelf or coffee-table top and so on).

To turn to FIG. 3, it shows a process 100 characterized by various non-limiting ways of producing the inventive product 10. At some original time a supply of plush articles 102 are obtained for inputting to the process 100. The coating activity 104 can be achieved preferably by such alternate ways as a dip coating process $104^1$ or else a spray coating process $104^2$. By either dipping or spraying, a coating 12 can be achieved in whole or in part. Needless to say that for various ones of the preferred materials for the coating 12 identified above, the dipping or spraying activities $104^1$ or $104^2$ require elevating the temperature of the material at some elevated temperature so that it liquefies. At the completion of the coating process 104, the coated article 105 can be set aside in a room-temperature environment to cool and harden.

FIGS. 1 and 2 show a plush article 10 and/or 10' which has been dipped in its entirety into a container of the chosen coating material. To return to the matter of the thick wax base 14, these articles 10 and/or 10' shown in FIGS. 1 and 2 were dunked completely in the chosen coating material and the set to dry on a surface for the purpose, such as a tray set in a drying rack or the like. The thick wax base 14 is a result of wet wax pooling and then drying. If it were intended to eliminate the thick wax base 14, there are several ways to achieve that. These include choosing a coating material which runs off and does not form such a base, or hanging the dipped or dunked article 105 to dry, or even by spray coating $104^2$ the input article 102 only lightly and so on.

The step(s) 108 of imbuing the scenting or fragrant substance(s) 106 to the coating 12 include alternative ways such as a process $108^1$ of pre-mixing the scenting or fragrant substance(s) 106 into the dipping container along with the chosen coating material. FIG. 3 shows that pre-mixing $108^1$ the scenting or fragrant substance(s) 106 into the coating material can be achieved regardless if the coating process 104 is dip coating $104^1$ or spray coating $104^2$. Likewise, an alternative way of imbuing 108 the scenting or fragrant substance(s) 106 into the coating 12 of the "at least" coated article 105 can be achieved regardless if the coating process 104 is by dip coating $104^1$ or spray coating $104^2$. That is, while the wax is still warm on the coated toy article 105, the scenting or fragrant substance(s) 106 can be "infused" after the fact into the coating 12 on the coated article 105 as by wet or aerosol spraying, or alternatively by dipping (dunking) the warm article 105 into containers of such scenting or fragrant substance(s) 106. In FIG. 3 this is indicated as the infusion process 108². That way, the scenting or fragrant substance(s) 106 are afforded a time slot to infuse or absorb into the warm wax coating 12 of article(s) 105 before the article 105's coating 12 cools too much and becomes relatively more resistant to the infusion and/or absorption actions 108². Again, in situations with the warm wax on article 105, the warm wax will still absorb or otherwise pick up or become infused with the scenting or fragrant substance(s) 106, even after the step of coating 104. Whether a producer prefers to utilize the pre-mixing process 108¹ or the infusing process 108² depends in part on the chosen scenting or fragrant substance(s) 106.

Example scenting or fragrant substance(s) 106 suitable for the purpose include without limitation various scented, fragrant or aromatic liquids and solids. Preferred scenting or fragrant substance(s) would comprise a group chosen from essential oils, perfume oils, extracts which emit a scent, fragrance, aroma or perfume regardless whether such extracts are alcohol-based or otherwise, such as glycerin-based as is known in the art. Indeed, evenly relatively finely pulverized solid materials such as salts, hard resins, or wood chips/dust can be pre-mixed as by stirring or agitating into a container of dip-coating material or else combined with an atomized or squirting stream of spray-coating material. Given the foregoing, persons having ordinary skill in the art will readily appreciate that routine trial and error affords ample opportunities to combine various diverse compounds of scenting or fragrant substance(s) to work toward any desired end result.

To summarize, the scenting or fragrant substance(s) 106 can be mixed in with warm wax or whatever chosen coating material is utilized either at a time before the coating 12 is administered or at a time preferably soon thereafter. In cases of warm wax, such warm wax will absorb or otherwise pick up or become infused with many scenting or fragrant substance(s) even after the step of coating 104.

Hence there is some time after the step of coating 104 the input plush article 102 to administer a further application to the coated article 105 of substances 106 by an infusion process 108² or the like, wherein such substances 106 comprise, namely, a selected or combination of scenting or fragrant substance(s) 106.

Given the above, the end result or output 10 of such process(es) 100 as shown by FIG. 3 achieves a scented waxed plush toy or article 10 and/or 10' in accordance with the invention as shown for example by FIG. 1 or 2. The scented waxed plush article 10 in accordance with the invention provides its owner with a novel accessory for freshening or scenting the air in a room or like space in combination with disguising the source thereof. Unknowing guests who encounter the enjoyable whiff of such scent, fragrance, aroma or perfume might first search for the source to be some candle or pot and the like. It should come as a novel surprise and/or matter of amusement to discover or be informed of the true source.

The scent-emitting power of the scented waxed plush article 10 in accordance with the invention naturally declines with age. However, for a certain number of times, users can re-invigorate the scent-emitting power by mildly warming up such an aging scented waxed plush article 10. This can be readily achieved with a conventional hair dryer among other ways to do so.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. A combination of a soft-sided plush article with a hard wax coating therefor, comprising;
   a plush article produced with a soft-sided casing made up as forming one or more soft-sided sacks, and further produced by having unconsolidated in-fill material filling out the sacks; combined with a coating of h wax first applied melted and then allowed to harden over the plush article in order to immobilize the soft-sided casing into one given posture or position of repose; and further comprising a scent substance which is imbued in the wax and which diffuses therefrom over time such that said combination doubles as an ornamental accessory as well as a disguised air freshener.

2. The combination of claim 1 wherein the unconsolidated in-fill material comprises any of natural pellets, synthetic pellets, beans, seeds, sawdust, straw, excelsior grass, polyfill or fiberfill.

3. The combination of claim 1 wherein the plush article's casing includes a velvety, fuzzy or furry appearance.

4. The combination of claim 1 wherein said coating of wax is further comprising a thick wax base layer providing a flat bottom for setting on planar support surfaces and providing the combination with a low-center of gravity and hence stability for propping up the combination in the given posture or position of repose.

5. The combination of claim 1 wherein the scent substance comprises any of perfume oils, alcohol- or glycerin-based extracts, or finely pulverized solid materials.

6. The combination of claim 1 further comprising wearing apparel adorned over the scented wax coating for further ornament.

7. A method of producing a scented waxed plush article comprising the steps of:
   producing a plush article that has a soft-sided casing which comprises a synthetic or natural textile or fur and which casing is made up to form one or more soft-sided sacks, said plush article being further produced with loose stuffing material for filling out the sacks;
   applying a coating of hot melted wax over the plush article and then posturing or posing the melted-wax covered plush article for subsequent cooling and solidifying of the wax such that the soft-sided casing is thereafter immobilized by the solidified wax into one given posture or position of repose; and
   imbuing the wax with a scent substance that diffuses such scent over time such that the scented waxed plush article doubles as an ornamental accessory as well as an air freshener.

8. The method of claim 7 wherein the step of applying a coating comprises either dipping said article in hot melted wax or spraying on hot melted wax in order to coat said article in whole or in part.

9. The method of claim 7 wherein the step of imbuing the wax with said scent substance comprises either pre-mixing the scent substance with the hot melted wax before the step of applying a coating or, else infusing the scent substance in the wax at elevated temperature so that the wax better accepts the infusion of the scent substance.

10. The method of claim 7 wherein the casing includes a velvety, fuzzy or furry finish.

11. The method of claim 7 further comprising during the step of posturing or posing the plush article, resting the melted-wax coated plush article on a planar work surface and allowing a thick wax base layer to pool around and harden such that the end-product scented waxed plush article is provided with a flat bottom for setting on planar support surfaces and weighted base of wax providing a low-center of gravity and hence stability for propping up the plush article in the given position of repose.

12. The method of claim 7 wherein:
the step of imbuing the wax with said scent substance combines with the step of the cooling and solidifying of the melted-wax over the covered plush article by a process of infusion.

13. The method of claim 12 wherein said process of infusion of the scent substance further comprises spraying an aerosol or liquid form of the scent substance onto the cooling and solidifying melted-wax.

14. The method of claim 7 further comprising, after an extended aging period for the scented waxed plush article following the final step, a step of re-invigorating scent-diffusion power of said scented waxed plush article by mildly warming up the wax coating thereof, including by means of a conventional hair dryer.

15. An air freshener disguised as an ornamental accessory comprising:
core comprising a filled casing wherein said casing is produced from a natural or synthetic textile or fur as well as is also produced to form at least one sack, said core further comprising unconsolidated in-fill material which is filled into said sack;
a coating of hard wax for the core applied over all or part of the casing; and
a scent substance imbued in the wax coating to diffuse over time such that said plush article thereby doubles as an ornamental accessory as well as a disguised air freshener.

16. The air freshener of claim 15 further comprising wherein said coating of hard wax includes portions covering al or part of the core's casing as well as includes another portion comprising a thick wax base layer providing a flat bottom for setting on planar support surfaces and providing said air freshener disguised as an ornamental accessory with a low-center of gravity and hence stability for propping up said plush article in a given posture or other position of repose.

17. The air freshener of claim 15 wherein the scent substance comprises any of perfume oils, alcohol- or glycerin-based extracts, or finely pulverized solid materials.

18. The air freshener of claim 15 wherein said plush article comprises a design realistically or otherwise imitating a plant, animal or human form.

* * * * *